United States Patent [19]

Habib

[11] Patent Number: 4,534,767

[45] Date of Patent: Aug. 13, 1985

[54] PROTECTIVE SEALING COMPOSITION IN MOLDED FORM

[75] Inventor: Wagdi W. Habib, Roselle, Ill.

[73] Assignee: Hollister Incorporated, Libertyville, Ill.

[21] Appl. No.: 272,191

[22] Filed: Jun. 10, 1981

Related U.S. Application Data

[63] Continuation-in-part of Ser. No. 185,003, Sep. 8, 1980, abandoned, which is a continuation-in-part of Ser. No. 90,855, Nov. 2, 1979, abandoned.

[51] Int. Cl.³ ............................................. A61F 5/44
[52] U.S. Cl. .................................... 604/336; 128/156
[58] Field of Search ............... 128/283, 156; 604/336; 536/114; 252/315-317

[56] References Cited

U.S. PATENT DOCUMENTS

| | | | |
|---|---|---|---|
| 3,302,647 | 2/1967 | Marsan | 128/283 |
| 3,640,741 | 2/1972 | Etes | 128/283 |
| 3,954,105 | 5/1976 | Nordby | 128/275 |
| 3,980,084 | 9/1976 | Kross | 128/283 |
| 4,253,460 | 3/1981 | Chen et al. | 128/283 |
| 4,254,008 | 3/1981 | Krsek | 260/33.4 R |

*Primary Examiner*—Teddy S. Gron
*Assistant Examiner*—T. J. Wallen

[57] ABSTRACT

Protective sealing compositions in the form of molded rings or sheets, which comprise gelled mixtures of water-absorbing particulate hydrocolloid gum and non-toxic liquid polyhydroxy alcohol are provided with increased resistance to the drained fluid (viz. urine or intestinal fluids) by incorporating a small amount of colloidal silica. Fumed silica is preferred. By limiting the amount of silica added appreciable reductions in the wet tack and/or dry tack of the composition can be avoided. The compositions can be used with ostomy devices, wound drainage devices, and incontinence devices.

10 Claims, No Drawings

PROTECTIVE SEALING COMPOSITION IN MOLDED FORM

CROSS-REFERENCE

This application is a continuation-in-part of co-pending application Ser. No. 185,003 filed Sept. 8, 1980, now abandoned, which was a continuation-in-part of application Ser. No. 90,855, filed Nov. 2, 1979, and now abandoned.

BACKGROUND AND PRIOR ART

Protective sealing compositions in the form of molded rings or sheets for application around surgical fluid drainage openings are known. A common formulation for such compositions comprises a gelled mixture of karaya gum and glycerin. See, for example, U.S. Pat. Nos. 3,302,647 and 3,954,105. As described in the first-cited patent, where the drainage opening is a stoma, the karaya-glycerin sealing composition may be used in the form of a molded ring which is placed around the stoma between the gasket of the ostomy appliance and the body of the wearer. The purpose of the ring is to provide a protective seal, that is, it is desired to prevent the intestinal fluid or urine being discharged from the stoma from leaking around the ring so that all of the discharged fluid is collected in the bag or pouch of the ostomy appliance. The sealing ring also performs the function of protecting the skin area around the stoma from the irritating urine or intestinal fluid, which in the case of ileostomies may include gastric juices. As illustrated by the second of the above-cited patents, the karaya-glycerin composition may also be used in the form of a sheet or blanket. Such blankets may also be used around stoma openings, or as described in U.S. Pat. No. 3,954,105, they may be used around drainage openings associated with a wound or surgical incision.

Sealing compositions of the kind described preferably have an initial tackiness, usually referred to as "dry tack", so that they will provide an initial adhesive adherence to the skin around the drainage opening. It is particularly important that the compositions provide a high degree of adhesiveness while in contact with aqueous fluid. This is usually referred to as "wet tack". The hydrocolloid in the composition, such as karaya, absorbs water which causes the hydrocolloid to swell and to increase in tackiness. However, with continued exposure to the aqueous fluid, especially where the fluid is urine or an intestinal discharge containing gastric juices, the composition tends to break down, losing mechanical strength, and eventually becomes ineffective for its desired protective sealing function. In application, such sealing rings or blankets must be frequently replaced. It has been desired to increase the mechanical and/or adhesive endurance of such rings or blankets, but heretofore no satisfactory means has been provided for accomplishing this result.

SUMMARY OF INVENTION

The present invention is based in part on the discovery that a new and surprising result is obtained by the incorporation of a small amount of colloidal silica, which is preferably in the form of fumed silica, in protective sealing compositions, which are composed of a mixture of hydrocolloid gum and polyhydroxy alcohol. More specifically, the resistance of such compositions in the form of molded rings or sheets to degradation by intestinal fluids and/or urine is markedly increased by incorporating as small amount of fumed silica as 0.2%. At concentrations of silica above 4.0% the wet tack of the composition is reduced to such an extent that the composition is not effective. However, by limiting the amount of silica dispersed in the composition, the mechanical endurance of the composition can be increased without appreciably reducing its wet tack, and a satisfactory dry tack may also be obtained.

DETAILED DESCRIPTION

The present invention is applicable to protective sealing compositions prepared from gelled mixtures of a particulate hydrocolloid gum and a liquid polyhydroxy alcohol, which are capable of being formed into molded rings or sheets and set by gelation. Based on present usage, the hydrocolloid gum is preferably karaya gum, but other gellable hydrocolloid gums can be used as a partial or complete substitute for the karaya. Such gellable hydrocolloid gums include ghatti, zedou, tragacanth, gelatin, dextran, pectin, xanthane, and similar natural gums. Synthetic gums may be used, including sodium carboxymethylcellulose and hydroxyethyl cellulose. Such hydrocolloid gums are characterized by being polysaccharides, by being hydrophilic and water-absorbing, and by being gellable in admixture with glycerin or other polyhydroxy alcohol.

For the purpose of the present invention, the hydrocolloid gums are used in a fine particulate form (viz. as powders). Karaya gum, for example, is usually employed in a sufficiently fine state of subdivision that the powder will pass a 100 mesh or finer screen. The powdered gums as used are air-dry, that is, dry to the touch, but may contain some moisture, such as 10 to 18% by weight moisture.

The principal liquid component of the sealing composition is preferably a non-toxic liquid polyhydroxy alcohol. Based on present usage, glycerin is the preferred alcohol, but other polyhydroxy alcohols of similar properties can be used, such as, for example, propylene glycol, sorbitol, etc. Preferably, the polyhydroxy alcohol is not only non-toxic and non-irritating when applied to the skin, but, in addition, has a soothing or emollient action as provided bby glycerin or similar emollient polyhydroxy alcohols.

In preparing the sealing composition, a sufficient amount of the polyhydroxy alcohol is employed to form a flowable mix, which can be formed or molded into the desired ring or sheet shape, and then set by gelation. The relative proportions of the polyhydroxy alcohol and the hydrocolloid can be varied while still achieving these general results. If too small an amount of the alcohol is present, the mix will be too stiff for flowing into the mold, while if too much of the alcohol is present, the molded composition will be too soft and insufficiently gelled. In accordance with present practice in relation to mixes of karaya gum and glycerin, approximately equal parts by weight of the gum and the alcohol give good results, However, a moldable mix can be prepared using more or less of the glycerin or other polyhydroxy alcohol. In general, the mix may contain from 35 to 55% of the karaya or other hydrocolloid, and from 35 to 55% of glycerin or other polyhydroxy alcohol. As a more specific example, mixes can be prepared using portions within the range from 80 to 120 parts by weight of glycerin per 100 parts of karaya gum.

In accordance with the present invention, colloidal silica is incorporated in the sealing composition, the silica preferably being homogeneously dispersed therein. Fumed silica is preferred, although colloidal silica gel can also be used. The fumed silica is produced by flame hydrolysis of the silicon tetrachloride. It can be obtained from various manufacturers, including the "Cab-O-Sil" products of Cabot Corporation, Boston, Mass., and the "Aerosil" products of Degussa, Inc. New York, N.Y., U.S.A. These products are silicon dioxide in colloidal form having very high surface areas. For example, one suitable specific product is the Grade M-5 of Cab-O-Sil.

In the broadest aspect of this invention, colloidal silica is incorporated in the composition in an amount of from 0.1 to 4.0% by weight. (This and other stated percentages are based on the total weight of the composition, including the silica and all other ingredients of the finished product.) Within the stated range the endurance of the gel composition in contact with urine and/or intestinal fluids is markedly increased while the wet tack adhesive property remains adequate. However, it is preferable not to use over 1.5% silica (viz. from 0.1 to 1.5%) so that the dry tack and wet tack properties are more fully retained.

To reduce the viscosity of the mix, and to facilitate its molding or forming, it has been found desirable to incorporate sodium carboxymethylcellulose (CMC) in the mix. For example, from 2 to 15% of CMC may be used. In representative formulations, from 3 to 8 parts by weight of CMC is combined with 40 to 50 parts each of karaya and glycerin, and from 0.5 to 1.2 parts of fumed silica. Where the CMC is omitted, the optimum amount of the fumed silica is somewhat lower, such as from 0.2 to 0.8% of the mix.

The compositions may include other minor ingredients, such as preservatives or antibacterial agents. For example, an alkyl para-hydroxy benzoate or a mixture of such benzoates, may be used as the preservative. For example, a mixture of methyl, ethyl, propyl, and butyl parabens can be used. Where parabens are employed, such as in amounts from 0.1 to 0.5%, it may be desirable to first dissolve the parabens in propylene glycol or other co-solvent with glycerin, in which the parabens are more soluble than in glycerin. For example, from 2 to 10 parts of propylene glycol can be used per 100 parts of glycerin.

In combining the ingredients to prepare the fluid molding composition, the parabens may first be dissolved in the small amount of propylene glycol, and then the propylene glycol solution of the paraben mixed with the larger amount of glycerin. The fumed silica can then be dispersed in the combined polyhydroxy alcohols by mixing until a uniform dispersion is obtained. The hydrocolloid gum powder is next added, and the mixing is continued until the composition is uniformly mixed. The composition is then molded prior to gellation, which may occur within 5 to 10 minutes. For molding, the composition can be poured into ring or sheet mold forms, and formed under light pressure to the desired shape, such as by use of a movable mold die or platen as the upper mold member. During the molding process, the composition will set up rapidly to a gel state. Where desired, gelation can be promoted by heating the composition, either in the mold, or subsequent to molding. For example, microwave heating may be applied to the composition in the mold, or the formed rings or sheets may be passed through an infrared heating tunnel. The temperature of heating is not highly critical, since gelation will occur and become completed at room temperature. However, by heating the molded sheets or rings to a temperature of about 160° to 180° F., completion of the setting and gelation occurs in a shorter time. During the setting, there is ordinarily no loss of the polyhydroxy alcohol, and therefore the composition should not be heated to a temperature above the boiling point of the polyhydroxy alcohol.

The practice of the present invention in preferred embodiments and the results obtained thereby are further illustrated by the following examples.

EXAMPLE I

In a presently preferred embodiment, a protective sealing composition is prepared in accordance with the present invention using the following formula.

FORMULA A

| Ingredients | Weight % |
| --- | --- |
| (1) 2% fumed silica[a] in glycerin blend[d] | 50.0 |
| (2) Karaya gum powder[b] | 45.0 |
| (3) Sodium Carboxymethylcellulose (CMC)[c] | 5.0 |
| | 100.0 |

[a]Provides 1% fumed silica, Cab-O-Sil M-5 (Cabot Corporation, Boston, Massachusetts).
[b]Smaller than 140 mesh; 10 to 18% moisture.
[c]CMC 7HOX8F (Hercules, Incorporated, Wilmington, Delaware).
[d]Glycerin Blend: 94.795% glycerin, 4.839% propylene glycol, 0.161% methylparaben, 0.028% propylparaben, and 0.177% butylparaben.

In compounding the above ingredients, the glycerin blend with the fumed silica uniformly dispersed therein is mixed with the karaya gum powder and the sodium carboxymethylcellulose until a uniform gellable mixture is obtained. This mixture, prior to gellation, is poured into molds for forming rings or sheets, and is cured in the molds to produce the ring or sheet product. The curing may be obtained by leaving the composition in the molds overnight at ambient room temperature. Alternatively, the curing may be accelerated by apply heat from infrared lights or microwave radiation. Microwave heating is preferred.

To improve dry tack, if desired, a small amount of a suitable pressure sensitive adhesive is deposited in the bottoms of the molds before filling them with the mix. For example, the adhesive may be the "H49" vinyl acrylic medical pressure-sensitive adhesive of U.S. Adhesives, Chicago, Ill., U.S.A.

EXAMPLE II

In another embodiment, a protective sealing composition is prepared in accordance with the present invention using the following formula.

FORMULA B

| Ingredients | Weight % |
| --- | --- |
| (1) Propylene glycol (USP) | 2.250 |
| (2) Methylparaben | 0.075 |
| (3) Propylparaben | 0.013 |
| (4) Butylparaben | 0.082 |
| (5) Glycerin (USP, 99%) | 46.580 |
| (6) Fumed silica | 0.500 |
| (7) Karaya gum powder | 50.500 |
| | 100.000 |

In compounding the above ingredients, ingredients (2) to (4), the parabens, are dissolved in ingredient (1), the propylene glycol. This solution is added to ingredient (5), the glycerin, and mixed until uniform. Ingredient (6), the fumed silica, is then dispersed in the liquid solution of the preceding ingredients, and the dispersion is mixed until uniform. The karaya powder, ingredient (7), is then added with mixing continued until a uniform gellable mixture is obtained. This mixture, prior to gellation, is poured into molds for forming rings or sheets, and is cured in the molds to produce the ring or sheet product. The curing may be obtained by leaving the composition in the molds overnight at ambient room temperature. Alternatively, the curing may be accelerated by applying heat from infrared lights or by microwave radiation.

In the foregoing example, the fumed silica is Cab-O-Sil M-5 (Cabot Corporation, Boston, Mass.). The gum karaya is in the form of a powder passing a 140 mesh screen, and may contain from 10 to 18% moisture.

EXAMPLE III

A composition is prepared as described in Example II except that algin powder is substituted on an equal weight basis for the karaya gum powder. The algin is supplied by Kelco Company, Clark, N.J.

EXAMPLE IV

Using the compounding procedure described in Example II, a protective sealing composition is prepared according to the following formula.

| FORMULA C | |
|---|---|
| Ingredients | Weight % |
| (1) Propylene glycol (USP) | 2.880 |
| (2) Methylparaben | 0.098 |
| (3) Propylparaben | 0.017 |
| (4) Butylparaben | 0.105 |
| (5) Glycerin (USP, 99%) | 56.400 |
| (6) Fumed silica | 0.500 |
| (7) Xanthan gum | 40.000 |
| | 100.000 |

In the foregoing formula, the xanthan gum is a food grade product supplied by Kelco Company, Clark, N.J.

EXAMPLE V

A protective sealing composition is prepared using the compounding and molding procedure of Example II, as applied to the following formula.

| FORMULA D | |
|---|---|
| Ingredients | Weight % |
| (1) Propylene glycol (USP) | 2.370 |
| (2) Methylparaben | 0.079 |
| (3) Propylparaben | 0.014 |
| (4) Butylparaben | 0.087 |
| (5) Glycerin (USP, 99%) | 46.450 |
| (5A) Sorbitol (USP, 70%) | 5.000 |
| (6) Fumed silica | 1.500 |
| (7) Gum zedou powder | 44.500 |
| | 100.000 |

In mixing the foregoing ingredients, ingredients (5) and (5A), the glycerin and sorbitol, are combined as described for the glycerin, ingredient (5), in the procedure of Example I.

EXAMPLE VI

A protective sealing composition is prepared according to the compounding procedure of Example II using the formula set out below.

| FORMULA E | |
|---|---|
| Ingredients | Weight % |
| (1) Propylene glycol (USP) | 3.05 |
| (2) Methylparaben | 0.10 |
| (3) Propylparaben | 0.02 |
| (4) Butylparaben | 0.11 |
| (5) Glycerin (USP, 99%) | 59.72 |
| (6) Fumed silica | 2.00 |
| (7) Sodium Carboxymethylcellulose | 35.00 |
| | 100.000 |

The sodium carboxymethylcellulose is CMC 7HOXF, supplied by Hercules, Incorporated, Wilmington, Del. The molded rings or sheets are preferably cured by microwave heating.

EXAMPLE VII

A protective sealing composition was prepared according to the following formula.

| FORMULA F | |
|---|---|
| Ingredients | Weight % |
| (1) Propylene glycol (USP) | 2.710 |
| (2) Methylparaben | 0.090 |
| (3) Propylparaben | 0.020 |
| (4) Butylparaben | 0.100 |
| (5) Glycerin (USP, 99%) | 53.080 |
| (6) Deionized water | 3.000 |
| (7) Fumed silica | 1.000 |
| (8) Sodium Carboxymethylcellulose | 15.000 |
| (9) Gum karaya powder | 25.000 |
| | 100.000 |

In compounding the above ingredients, the same mixing procedure is used as described in Example II with reference to ingredients (1) to (5). Ingredient (6), the deionized water is then added, and the mixing is continued to produce a uniform mixture. Ingredient (7), the fumed silica, is then dispersed in the liquid solution to form a uniform dispersion. Ingredient (8), the sodium carboxymethylcellulose is then added with continued mixing, and ingredient (9), the karaya is added last, and the mixing continued until a uniform gellable composition is obtained. The molding and gelling procedure is the same as described in Example II.

EXAMPLE VIII

Endurance and tack tests were conducted using the base formula set out below and amounts of fumed silica (Cab-O-Sil M-5) from 0 to 2.5%.

| BASE FORMULA | |
|---|---|
| Ingredients | Parts by Weight |
| (1) Propylene glycol (USP) | 0.735 |
| (2) Methylparaben | 0.098 |
| (3) Propylparaben | 0.029 |
| (4) Butylparaben | 0.049 |
| (5) Glycerin (USP, 99%) | 49.040 |
| (6) Fumed silica | 0 to 2.500 |
| (7) Karaya gum powder | 50.000 |

For the endurance tests, the simulated intestinal fluid was prepared as described in *U.S.P. XIX* "Intestinal Fluid, Simulated, TS," pg. 765 (1974). The simulated urine was prepared as described in *Remington's Pharameceutical Sciences*, "Urine," pg. 598–9, Ed 15 (1975). The dry and wet tack tests were conducted by a modification of the ASTM Method 02979-71, using a probe of 0.5 cm diameter.

The endurance test apparatus includes a tank for containing the simulated intestinal fluid or urine, and a plurality of tripod testing fixtures, which may be placed in the tank in contact with the solution. The testing fixture has a platform at the top with a sample-receiving recess. The center portion of the recess is cut-out to provide an opening through the platform. When placed in test position, the test samples bridge the openings. U-shaped weights are then placed over the samples. These weights are in the form of steel hooks weighing approximately 7.4 grams. In use, the hooks are placed over the samples so that when the hooks break through the samples they would fall freely through the openings in the platforms. Nylon strings are attached to the upper cross-arm portions of the inverted U-shaped hooks and the strings are attached to the operating levers of micro switches, the lengths of strings being selected so that when the sample is broken, the micro switch will be activated, and a timing clock for the particular sample will be stopped. In starting the test, after the samples have been placed in the tank and the strings attached to the microswitch levers, the simulated urine or intestinal fluid is added to the tanks to a level above the position of the samples, and the timing clocks for each sample are started. The elapsed time for breakthrough of each sample is thereby automatically recorded.

The samples for the endurance tests were cut sections of rings molded from the formulas varying fumed silica content. Each test sample has a weight of approximately 1.0 grams, and had an elongated shape. The center portions of the samples engaged by the weighted hooks had dimensions of approximately 0.15 by 0.3 inches. The measured time for breakthrough was corrected by multiplying the measured time by 1.0 grams of the sample divided by actual weight of the sample. For the tack tests, cut sections of the rings were applied to test discs having a center opening through which the tack probe extends. Dry tack was determined with the surface of the sample in dry condition, and wet tack was determined after the sample had been contacted with water. The force required to separate the probe from the sample was measured in grams, and recorded as grams per centimeter of probe diameter, which was 0.5 cm. Replicate tests were conducted on each sample, and the values compiled as averages of five identical samples.

The results obtained by the endurance and tack tests are summarized below in Table A.

TABLE A

| % Fumed Silica | Endurance time in simulated Urine | Endurance time in simulated Intestinal Fluid | Tack (gms/05 cm) Dry | Wet |
| --- | --- | --- | --- | --- |
| None | 2.0 hrs. | 1.5 hrs. | 216 | 324 |
| 0.25% | Over 24 hrs. | 16.0 hrs. | 342 | 406 |
| 0.5% | 18.75 hrs. | Over 24 hrs. | 338 | 428 |
| 1.0% | Over 24 hrs. | Over 24 hrs. | 246 | 312 |
| 1.75% | Over 24 hrs. | Over 24 hrs. | 164 | 270 |
| 2.5% | Over 24 hrs. | Over 24 hrs. | 100 | 270 |

EXAMPLE IX

Further endurance and tack test were conducted using the base formula set out in Example I and the procedure therein. The silica was varied from 0.2 to 4.0% The total of the fumed silica and the glycerin blend was maintained at 50% by weight, the amount of the glycerin blend being correspondingly reduced as the amount of fumed silica was increased. The endurance times were measured on the basis of hours per gram of test sample, and the test samples were prepared with a diameter of 0.25 cm. The results obtained are summarized below in Table B.

TABLE B

| % Fumed Silica | Endurance Time (hrs/gm) Simul. Urine | Simul. Int. Fluid | Tack (gms/0.25 cm. dia) Dry | Wet |
| --- | --- | --- | --- | --- |
| 0.2 | 98.7 | 87.1 | 322 | 594 |
| 0.5 | 61.0 | 64.7 | 390 | 558 |
| 1.0 | 93 | 68 | 320 | 586 |
| 2.0 | 148.7 | 114.7 | 38 | 552 |
| 3.0 | 128.8 | 103.2 | 4 | 370 |
| 4.0 | 132 | 71.5 | 0 | 334 |

EXAMPLE X

In any formulation, where the molded ring or sheet has insufficient dry tack, a coating of a suitable pressure-sensitive adhesive can be applied to the side of the ring or sheet which will be pressed against the skin of the wearer. For example, a vinyl acrylic medical pressure-sensitive adhesive can be used, such as adhesive H49, supplied by U.S. Adhesives, Chicago, Ill. U.S.A. Alternatively, an adhesive may be incorporated in the mix before molding, for example, as a glycerin emulsion of the adhesive.

EXAMPLE XI

Compositions prepared in accordance with the present invention can also be used as pads or liners in male incontinence devices. (See U.S. Pat. No. 4,187,851.) A preferred formula for this type of composition is set out below.

| Preferred Formula Ingredients | Wt. % |
| --- | --- |
| Hydrocolloid | 15 to 25 |
| Polyhydroxy alcohol | 50 to 70 |
| Fumed Silica | 1 to 3 |
| Polyacrylamide resin | 5 to 20 |

In the above formula the hydrocolloid, polyhydroxy alcohol and fumed silica ingredients are as previously described. The polyacrylamide resin may be a "Reten" resin of Hercules, Incorporated, as described in U.S. Pat. Nos. 4,115,339 and 4,258,271. The cited patents also describe gamma irradiation cross-linking of such polyacrylamide resin. This can be a desirable procedure in preparing the material for incontinence device sealant pads or other uses.

An example of a specific formulation is as follows:

| Specific Formula Ingredients | Weight % |
| --- | --- |
| Karaya powder | 15.00 |
| Sodium carboxymethyl cellulose | 5.00 |
| Polyacrylamide (non-ionic) | 10.00 |
| Polyvinyl alcohol | 5.00 |
| Fumed silica | 2.00 |
| Glycerin | 59.73 |
| Propylene glycol | 3.05 |
| Methylparaben | 0.09 |
| Propylparaben | 0.02 |
| Butylparaben | 0.11 |

| Ingredients | Specific Formula Weight % |
|---|---|
| | 100.00% |

In compounding the foregoing ingredients, a mixture can first be prepared of the liquid ingredients (glycerin propylene glycol, and the parabens). The fumed silica is then dispersed in the liquid mixture, and thereafter the other powder ingredients are added (karaya, carboxymethyl cellulose, polyacrylamide, and polyvinyl alcohol). The completed mixture is then molded to form the pads or formed into sheets for use in preparing the pads. Either in pad or sheet form, the material can be subjected to gamma irradiation, preferably from a Cobalt-60 radiation source. The amount of radiation employed should be sufficient to sterilize the material, and to achieve crosslinking of the polyacrylamide resin. For example, a radiation level of 2.5 megarads is satisfactory.

I claim:

1. A protective sealing composition in the form of a molded gelled ring, sheet, or the like, said composition comprising essentially a gelled mixture of gellable, water-absorbing, particulate hydrocolloid gum and a non-toxic liquid polyhydroxy alcohol, wherein the improvement comprises having dispersed in said composition an amount of fumed silica within the range from 0.1 to 4.0% by weight, said amount of fumed silica being effective to increase appreciably the mechanical endurance of said sealing composition when exposed to urine or intestinal fluid.

2. The composition of claim 1 in which said silica is present in an amount from 0.1 to 1.5% by weight.

3. A protective sealing composition in the form of a molded gelled ring, sheet, or the like said composition comprising essentially a gelled mixture of karaya gum powder and a non-toxic liquid polyhydroxy alcohol, wherein the improvement comprises having dispersed in said composition an amount of fumed silica within the range from 0.1 to 4.0% by weight, said amount of fumed silica being effective to increase appreciably the mechanical endurance of said sealing composition when exposed to urine or intestinal fluid.

4. The composition of claim 3 in which said fumed silica is present in an amount from 0.1 to 1.5% by weight.

5. The composition of claim 3 in which said alcohol is glycerin, or a mixture of glycerin and propylene glycol.

6. The composition of claim 3 wherein the improvement further comprises having from 2 to 15% by weight of sodium carboxymethylcellulose in said composition.

7. A protective sealing composition in the form of a molded gelled ring, sheet, or the like, said composition comprising essentially a gelled mixture of a gellable, water-absorbing, particulate hydrocolloid and a nontoxic liquid polyhydroxy alcohol, wherein the improvement comprises having dispersed in said composition an amount of fumed silica within the range from 0.1 to 4.0% by weight together with from 2 to 15% by weight of sodium carboxymethylcellulose, said amount of fumed silica being effective to increase appreciably the mechanical endurance of said sealing composition when exposed to urine or intestinal fluid.

8. The composition of claim 7 in which said alcohol is glycerin, or a mixture of glycerin and propylene glycol and said hydrocolloid is karaya.

9. A protective sealing composition in the form of a molded gelled ring, sheet, or the like, said composition being composed essentially of a gelled mixture of karaya gum powder and glycerin, wherein the improvement comprises having dispersed in said composition an amount of from 0.1 to 1.5% by weight of fumed silica together with 3 to 8% by weight of sodium carboxymethylcellulose, said amount of fumed silica being effective to increase appreciably the mechanical endurance of said sealing composition when exposed to urine or intestinal fluid.

10. The compositions of claims 1, 3, 7 or 9 which also contain from 5 to 20% by weight of cross-linked polyacrylamide.

* * * * *